United States Patent [19]

Lokio et al.

[11] Patent Number: 5,684,183
[45] Date of Patent: Nov. 4, 1997

[54] METHOD FOR PREPARING 4-ALKYL-2-HYDROXY-3,5-DICHLOROBENZENE SULPHONIC ACIDS

[76] Inventors: Ari Lokio, Ansatie 4 C; Markku Niemi, Puutarhurintie 18-20 B, both of Espoo, Finland, FIN-02940; Elias Suokas, Hakamaki 2 E 70, Espoo, Finland, FIN-02120

[21] Appl. No.: 676,578

[22] Filed: Jul. 1, 1996

[30] Foreign Application Priority Data

Jul. 5, 1995 [FI] Finland .................... 953320

[51] Int. Cl.$^6$ .................... C07C 309/30
[52] U.S. Cl. .................... 562/78
[58] Field of Search .................... 562/78

[56] References Cited

FOREIGN PATENT DOCUMENTS 0 473 464 A1  3/1992  European Pat. Off. .
287 932 C     6/1928  Germany .

OTHER PUBLICATIONS

Chemical Abstracts, vol. 78 (1973), 97311y, Japan, Kokai 72 34, 326.
Chemical Abstracts, vol. 110 (1989), 10036v, Rev. Chim. (Bucharest) 1988, 39(6), 483–6.
Chemical Abstracts, vol. 101 (1984), 6245j, J. Chem. Soc., Perkin Trans. 2 1984, (3), 451–3.
Chemical Abstracts, vol. 98 (1983), 166687c, Chemosphere 1983, 12(2), 217–24.
Chemical Abstracts, vol. 98 (1983), 142706g, Curr. Sci. 1983, 52(3), 125–6.
Chemical Abstracts, vol. 95 (1981), 203456n, J. Indian Chem. Soc. 1981, 58(10), 985–8.
Chemical Abstracts, vol. 94 (1981), 15345f, J. Indian Chem. Soc. 1980, 57(6), 640–2.
Chemical Abstracts, vol. 92 (1980), 41478e, J. Indian Chem. Soc. 1979, 56(5), 518–20.
Chemical Abstracts, vol. 105, No. 15, 13 Oct. 1986, Columbus, Ohio, US: abstract No. 133507.
Chemical Abstracts, vol. 110, No. 7, 13 Feb. 1989, Columbus, Ohio, US; abstract No. 57298.

*Primary Examiner*—Nicky Chan
*Attorney, Agent, or Firm*—Ron Fish; Falk & Fish LLP

[57] ABSTRACT

The invention is related to a method for preparing 4-alkyl-2-hydroxy-3,5-dichlorobenzene sulphonic acids by sulphonating 4-chloro-3-alkylphenol and by chlorinating 4-alkyl-2-hydroxy-5-chlorobenzene sulphonic acid present in an acidic reaction mixture. According to the invention, chlorination is carried out by adding, to the acidic reaction mixture, salts of hypochlorous and/or chloric acids and, when needed, hydrochloric acid or its salt.

4 Claims, No Drawings

METHOD FOR PREPARING 4-ALKYL-2-HYDROXY-3,5-DICHLOROBENZENE SULPHONIC ACIDS

The invention is related to a method for preparing 4-alkyl-2-hydroxy-3,5-dichlorobenzene sulphonic acids by sulphonating 4-chloro-3-alkylphenol and by chlorinating 4-alkyl-2-hydroxy-5-chlorobenzene sulphonic acid present in an acidic reaction mixture.

The 4-alkyl-2-hydroxy-3,5-dichlorobenzene sulphonic acids prepared by the method according to the invention are valuable raw materials in preparing photographic chemicals when the sulphonic acid group is replaced with a nitro group. This substitution reaction can be performed in a known manner by adding nitric acid to the chlorination reaction mixture without needing to isolate the dichloro compound between the steps.

The method according to the invention can be described by the following reaction sequence:

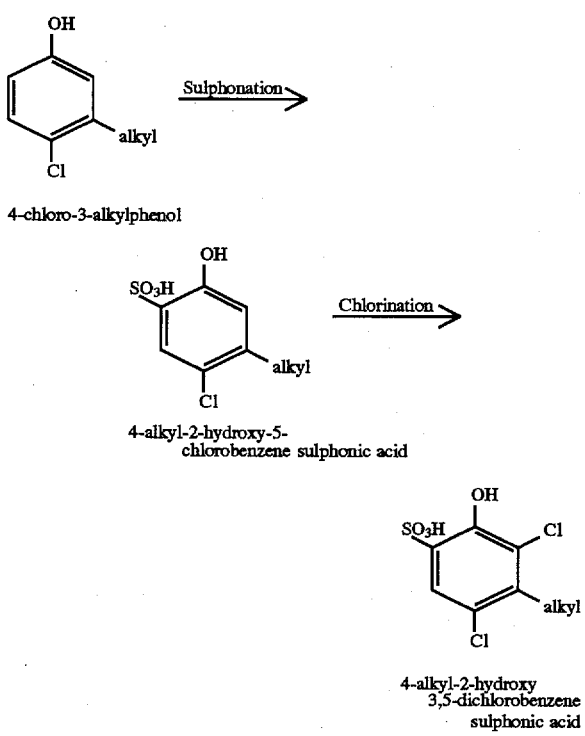

The alkyl is preferably methyl, ethyl or isopropyl.

It is already known how to sulphonate 4-chloro-3-alkylphenol by using different sulphonation reagents. In the method according to U.S. Pat. No. 5,136,109 and the corresponding EP application 473 464, sulphonation is carried out by using chloro-sulphonic acid in organic solvent after which water is added to the reaction mixture, and the chlorination of 4-alkyl-2-hydroxy-5-chlorobenzene sulphonic acid is carried out by using a compound of hydrochloric acid and hydrogen peroxide with or without a catalyst, whereby the chlorine needed in the chlorination is generated in the reaction mixture in situ.

Sulphonation has also been carried out by using an excess amount of concentrated sulphuric acid, as disclosed in JP application 61-57536, and by sulphuric anhydride complex as disclosed in U.S. Pat. No. 3,903,178. The usage of chlorine and sulphuryl chloride in chlorination is disclosed in various publications such as EP application 473 464 which uses these chlorination reagents in the comparison.

The above-mentioned known methods are functional as such but they have disadvantages. When elemental chlorine and sulphuryl chloride are used for chlorination, only half of the available chlorine is used. In addition to this, an equivalent mount of hydrogen chloride is generated as a byproduct and an equivalent mount of sulphur dioxide is generated from sulphuryl chloride. To handle these gases, a separate equipment is needed so that the gases are not emitted into the environment. When hydrogen peroxide is used, no byproducts are generated but because hydrogen peroxide and hydrochloric acid (in an excess amount) are added as an aqueous solution, it brings water to the reaction mixture and, in addition, this method requires special arrangements for handling the hydrogen peroxide safely. None of the above-mentioned methods use the residual sulphuric acid from the sulphonation.

The object of the present invention is to provide a method for preparing 4-alkyl-2-hydroxy-3,5-dichlorobenzene sulphonic acids by sulphonating 4-chloro-3-alkylphenol and by chlorinating the 4-alkyl-2-hydroxy-5-chlorobenzene sulphonic acid present in the obtained acidic reaction mixture so that the chlorination reagents can be utilised as effectively as possible, while the residual sulphuric acid, present in the acidic reaction mixture obtained as a result of the sulphonation, can also be utilised.

According to the present invention, chlorination is carded out by adding, to the acidic reaction mixture, salts of hypochlorous and/or chloric acids and, when needed, hydrochloric acid or its salt The chlorination reagent is thus generated in situ in the reaction mixture by the oxidising effect of the salts of hypochlorous and/or chloric acids by utilising the acidity of the reaction mixture and the chlorine in the oxidising reagent. When chlorate is used, the chloride ions in the reaction mixture are also used. Chloride ions can also be used when obtained from salts, whereby the cationic moiety neutralises some of the excess acid of the mixture. Consequently, an inexpensive chloride source can be used in the method, for example, sodium chloride whose chlorine is used in the chlorination while the sodium neutralises the sulphuric acid.

Sodium or potassium chlorate or hypochlorite are preferably used as chlorination reagent. In addition, one or more of the following may be added to the reaction mixture: sodium chloride, potassium chloride, calcium chloride, aluminum chloride, and iron chloride.

The invention is described in detail with the aid of examples which by no means limit the scope of the invention. Isolation of the product, the 4-alkyl-2-hydroxy-3,5-dichlorobenzene sulphonic acid, is normally not practical because nitration can be carried out in the chlorination mixture and isolation would only cause reduced yield. For the analyses, the product was isolated only in examples 2a and 12, and the isolated products were used as reference substances for the analysis of the other examples. The yield was measured from 3-alkyl-4-chlorophenol. All the percentages are given in % by weight if not otherwise stated.

EXAMPLE 1

Preparation of the Starting Material (Alkyl=Ethyl) by Sulphonating with Oleum 47.0 g of 3-ethyl-4-chlorophenol was dissolved in 120 ml of 1,2-dichloroethane. 82 g of 30-% oleum was added to the mixture during one hour and the temperature was kept at 20°–25° C. The mixture was stirred for 2 hours at this temperature. According to a liquid chromatogram, the starting material had reacted completely. The obtained 4-ethyl-2-hydroxy-5-chlorobenzene sulphonic acid mixture was used as the starting material in the subsequent reactions.

EXAMPLES 2a AND 2b

Chlorination by Hydrochloric Acid and Chlorate Salt a) 31.3 g of 3-ethyl-4-chlorophenol was dissolved in 1,2-dichloroethane and sulphonated in the manner according to Example 1. 20 ml of water and 73 g of 30-% hydrochloric acid and 53 g of 20-% $NaClO_3$ solution were added to the mixture during 45 minutes at about 20° C. According to a liquid chromatographic analysis, the chlorination was complete. 50 ml of water was added to the mixture and the precipitate was filtered and washed with dichloroethane. 26.6 g of dry precipitate was obtained and it contained 81% of 4-ethyl-2-hydroxy-3,5-dichlorobenzene sulphonic acid, $C^{13}NMR$ (DMSO solvent and reference 39.5): 12.2 ($CH_3$); 24.7 ($CH_2$); 121.4 (C-3); 122.3 (C-5); 125.3 (C-6); 130.4 (C-1); 141.2 (C-4); 148.7 (C-2); IR: 3376, 1404, 1251, 1211, 1133, 1048, 1041 (and 1186 sodium sulphate). The rest of the precipitate was sodium sulphate.

b) 4 ml of water and then 5 ml of 37-% hydrochloric acid were added to the reaction mixture (55 g) of Example 1, holding the mixture to below 30° C. 52.7 g of 7-% $KClO_3$ solution was gradually added to this mixture, keeping the temperature at about 25° C. After 2.5 hours, 80% of the starting material had reacted. 1.2 g of 37-% hydrochloric acid was added to the mixture and slitting was continued overnight after which the yield of 4-ethyl-3-hydroxy-3,5-dichlorobenzene sulphonic acid was 97%.

EXAMPLE 3

Chlorination by Sodium Chloride and Sodium Chlorate 4 ml of water and, then, 23.4 g of 20-% NaCl solution were added to the reaction mixture (55 g) of Example 1, keeping the temperature to below 30° C. The mixture was diluted with 20 ml of water. 21.3 g of 20-% $NaClO_3$ solution was added to the minus, keeping the temperature at about 30° C. After stirring overnight at room temperature, the yield of dichloro mixture was 98%.

EXAMPLE 4

Chlorination by Potassium Chloride and Potassium Chlorate 4 ml of water and 29.8 g of 20-% KCl solution and then 70 g of 7-% $KClO_3$ solution were added to the mixture of Example 1 at a temperature of 25°–40° C. The mixture did not mix well and it reacted slowly. After mixing overnight, conversion was 73%. 13 ml of 37-% hydrochloric acid was added to the mixture and stirring was continued for 3.5 hours at 40° C., after which the yield of dichloro mixture was 92%.

EXAMPLE 5

Chlorination by Sodium Hypochlorite 10 ml of water and 85 g of sodium hypochlorite solution containing 10% of active chlorine were added to the reaction mixture (55 g) of Example 1 at about 40° C. during 2 hours. Soon after the adding had been ended, the yield of the dichloro mixture was 95%.

EXAMPLE 6

Preparation of Starting Material (Alkyl=Ethyl) by Sulphonating with Sulphuric Acid 31.3 g of 3-ethyl4-chlorophenol was added to 118 g of 98-% sulphuric acid and it was stirred for 1.5 hours at 30° C. 40 ml of water was added to the mixture and the obtained 4-ethyl-2-hydroxy-5-chlorobenzene sulphonic acid mixture was used in the subsequent chlorination examples.

EXAMPLE 7

Chlorination by Hydrochloric Acid and Sodium Chlorate 6.5 g of 30-% hydrochloric acid and then 9.3 g of 20-% sodium chlorate solution were added to the sulphonation solution (38 g) of Example 6 during two hours, keeping the temperature at about 40° C. After the adding had been ended, the yield of 4-ethyl-2-hydroxy-3,5-dichlorobenzene sulphonic acid was 94%.

EXAMPLE 8

Chlorination by Sodium Chloride and Sodium Chlorate 15.7 g of 20-% sodium chloride solution and then 10 g of 20-% sodium chlorate solution were added to the sulphonation solution (38 g) of Example 6 at 40°. After 3 hours, the yield of the dichloro derivative was 95%.

EXAMPLE 9

Chlorination by Sodium Hypochlorite 10 ml of water and 57 g of sodium hypochlorite solution containing 10% of active chlorine were added to the sulphonation solution (38 g) of Example 6 at about 40° C. After three hours, the yield of the dichloro compound was 94%.

EXAMPLE 10

Chlorination by Calcium Chloride and Sodium Chlorate 20 g of 15-% calsium chloride solution and 10 g of 20-% sodium chlorate solution were added to the sulphonation solution (38 g) of Example 6. The temperature was maintained below 40° C. After two hours, the yield of the dichloro mixture was 92%.

EXAMPLE 11

A Reference Test by Hydrochloric Acid and Sodium Perchlorate 10 g of water and 7.9 g (7 ml) of 37-% hydrochloric acid were added to the mixture (55 g) of Example 1 at a temperature below 40° C. 8.7-% sodium perchlorate solution (56.2 g, 0.04 mol) was added to the mixture at 35° C. The starting material had not reacted at all at this temperature during two and a half hours.

EXAMPLE 12

Preparation of Starting Material (Alkyl=Methyl) and Chlorination by Hydrochloric Acid and Sodium Chlorate 28.8 g of 4-chloro-3-methylphenol was dissolved in 60 ml of 1,2-dichloroethane and 57.7 g of 30-% oleum was added to the mixture during two hours, keeping the temperature at 20°–25° C. After one hour of starting the starting material had reacted completely and 20 ml of water was added to the mixture during haft an hour and then 73 g of 30-% hydrochloric acid was added in 15 minutes at about 20° C. 53 g of 20-% $NaClO_3$ solution was added to the mixture in 70 minutes at 25° C. According to a liquid chromatographic analysis, the sulphonic acid had reacted completely and 50 ml of water was added to the mixture and the precipitated product was washed with dichloroethane and water, and 27.4 g of precipitate was recrystallised from the water (165 ml). The purity of the dried precipitate was over 98% (as determined by NMR): $C^{13}NMR$ (DMSO solution and ref. 39.5): 17.8 ($CH_3$); 122.1; 123,1; 125.2; 130.1; 136.2; 148.6 (carbons of the benzene ring). IR: 3191, 1444, 1345, 1269, 1131, 1048, 749, 606.

EXAMPLE 13

Preparation of Starting Material (Alkyl=Methyl) and Chlorination by Trichloride and Sodium Chlorate

EXAMPLE 15

Chlorination by Hydrochloric Acid and Sodium Chlorate (Alkyl=Isopropyl)

17.1 g of 3-isopropyl-4chlorophenol was dissolved in 30 ml of 1,2-dichloroethane and 27.5 g of 30-% oleum was added to the mixture during one hour, keeping the temperature at 20°–25° C. According to a liquid chromatographic analysis, the starting material had reacted completely after one hour of stirring. 10 ml of water was added to the mixture during 20 minutes and then 37 g of 30-% hydrochloric acid in 10 minutes at about 15° C. 26.5 g of 20-% $NaClO_3$ solution was added to the mixture in an hour and a half at 25° C. According to a liquid chromatographic analysis, the sulphonic acid had reacted completely after the mixture had been stirred for half an hour at 25° C. 20 ml of water was added to the mixture and the precipitated product was washed with dichloroethane and water. 2-hydroxy-4-isopropyl-3,5-dichlorobenzene sulphonic acid, isolated as sodium salt, was dried overnight at 23° C. and its purity was 90% (4.5% by weight of $H_2O$) as determined by NMR: $C^{13}$NMR (Ref. TMS 0.0) 19.1: 30.9; 121.7; 122.4; 126.5; 130.3; 143.4; 148.9. IR: 3570, 3320, 1403, 1355, 1237, 1181, 1045, 674, 641, 607, 568, 540.

EXAMPLE 16

Chlorination by Hydrochloric Acid and Impure (10% NaCl) Sodium Chlorate 17.1 g of 34isopropyl-4-chlorophenol was dissolved in 30 ml of 1,2-dichloroethane and 26.7 g of 30-% oleum was added to the mixture during one hour, keeping the temperature at 20°–25° C. After 2 hours of stirring, the starting material had reacted completely. 10 ml of water was added to the mixture during 15 minutes, cooling it, and 37 g of 30-% hydrochloric acid was added during one hour. Thereafter, 20-% $NaClO_3$ solution (totalling 27 g) was added to the mixture during one hour and 15 minutes at 25° C., the solution comprising 0.53 g of NaCl as an impurity (10% by weight as compared with sodium chlorate). The reaction mixture was stirred for another 2 hours at 25° C., and the mount of the thus created dichloro compound was analysed by using the product of Example 15 as a standard; the non-isolated yield was 70%.

What is claimed is:

1. A method for preparing 4-alkyl-2-hydroxy-3,5-dichlorobenzene sulphonic acids by sulphonating 4-chloro-3-alkylphenol and by chlorinating 4-alkyl-2-hydroxy-5-chlorobenzene sulphonic acid present in an acidic reaction mixture, characterized in that chlorination is carried out by adding, to the acidic reaction mixture, salts of hypochlorous and/or chloric acids and, optionally, hydrochloric acid or its salt.

2. A method according to claim 1, characterized in that sodium or potassium chlorate or hypochlorite are used as the chlorination reagent.

3. A method according to claim 1, characterized in that, in addition to the salt of chloric acid, one or more of the following are added to the acidic reaction mixture: NaCl, KCl, $CaCl_2$, $AlCl_3$, $FeCl_3$, and HCl.

4. A method according to claim 2, characterized in that, in addition to the salt of chloric acid, one or more of the following are added to the acidic reaction mixture: NaCl, KCl, $CaCl_2$, $AlCl_3$, $FeCl_3$, and HCl.

* * * * *